United States Patent
Kahn et al.

(10) Patent No.: US 8,491,120 B2
(45) Date of Patent: Jul. 23, 2013

(54) RETINAL FUNDUS SURVEILLANCE METHOD AND APPARATUS

(75) Inventors: David Alexander Kahn, Ottawa (CA); Ian Powell, Ottawa (CA)

(73) Assignee: Annidis Health Systems Corp., Ottawa, Ontario (CA)

( * ) Notice: Subject to any disclaimer, the term of this patent is extended or adjusted under 35 U.S.C. 154(b) by 277 days.

(21) Appl. No.: 12/988,887

(22) PCT Filed: Apr. 22, 2009

(86) PCT No.: PCT/CA2009/000540
§ 371 (c)(1),
(2), (4) Date: Oct. 21, 2010

(87) PCT Pub. No.: WO2009/129624
PCT Pub. Date: Oct. 29, 2009

(65) Prior Publication Data
US 2011/0043756 A1    Feb. 24, 2011

Related U.S. Application Data

(60) Provisional application No. 61/046,924, filed on Apr. 22, 2008.

(51) Int. Cl.
*A61B 3/14* (2006.01)
*A61B 3/00* (2006.01)

(52) U.S. Cl.
USPC ............ 351/206; 351/200; 351/210; 351/246

(58) Field of Classification Search
USPC .......................... 351/205–206, 210, 200, 246
See application file for complete search history.

(56) References Cited

U.S. PATENT DOCUMENTS

| | | | |
|---|---|---|---|
| 5,539,517 A | 7/1996 | Cabib | |
| 5,784,162 A * | 7/1998 | Cabib et al. | 356/456 |
| 6,142,629 A | 11/2000 | Adel | |
| 6,276,798 B1 | 8/2001 | Gil | |
| 6,992,775 B2 | 1/2006 | Soliz | |
| 2005/0288565 A1 | 12/2005 | Kerr | |
| 2008/0007692 A1 | 1/2008 | Mihashi | |
| 2009/0153797 A1* | 6/2009 | Allon et al. | 351/206 |

FOREIGN PATENT DOCUMENTS

| WO | 95/28125 | 10/1995 |
|---|---|---|
| WO | 02/087427 | 11/2002 |

OTHER PUBLICATIONS

European Patent Application No. 09734045.9, Extended European Search Report dated Sep. 28, 2012.

* cited by examiner

*Primary Examiner* — Dawayne A Pinkney
(74) *Attorney, Agent, or Firm* — Mukundan Chakrapani; Borden Ladner Gervais LLP

(57) ABSTRACT

A method and apparatus for quantitatively imaging the retinal fundus. The method for retinal health assessment comprises imaging the retinal fundus of a patient's eye at different wavelengths within a spectral range and determining spectral reflectivity of the retina for each pixel within a field of view (FOV). The retinal health is assessed based on the spectral reflectivity of the retina. The metabolic and anatomical activity of the eye is monitored to detect, at the earliest stage, activity that could lead to the onset of blinding eye diseases such as macular degeneration, diabetic retinopathy, glaucoma, cataracts, etc.

20 Claims, 10 Drawing Sheets

SECTION A-A

RETINAL FUNDUS SURVEILLANCE METHOD AND APPARATUS

FIELD OF THE INVENTION

The present invention relates generally to a method and apparatus for imaging the retinal fundus. More particularly, the present invention relates to a method and apparatus for quantitative imaging the retinal fundus.

BACKGROUND OF THE INVENTION

The fundus of the eye, or retina, is a complex layered structure arranged in an approximately spherical shape at the back of the eyeball. It contains the light sensing rods and cones that enable vision. It is nourished by oxygenated blood supplied through arterioles and removed through venules. The nerve impulses from the rods and cones are directed to the brain through the optic nerve on the fundus, corresponding to the blind spot.

Direct visual observation of the retinal fundus can be accomplished using an ophthalmoscope, an instrument that has been around in various forms for over 150 years. The ophthalmoscope employs a light source, means for coupling the light into the eye through the pupil, and means for collecting light reflected back from the fundus and presenting an image of the fund us to the observer. The eye responds to continuous light by constricting the pupil size and so reducing the amount of light available to form an image. For this reason, the eye pupil may have to be chemically dilated using a mydriatic.

A fundus camera is similar to the ophthalmoscope but provides a permanent record of the fundus image in the form of a photograph. It also enables the use of a short, powerful flash of light to replace the continuous light required for the ophthalmoscope, and so sometimes avoiding the need for a mydriatic. The fundus camera uses an electronic image sensor such as a charge-coupled device (CCD) and the image is stored electronically. It may be displayed on a monitor or printed out as a photograph.

The fund us image is dominated by the appearance of the optic nerve and the vascular structure of arterioles and venules. It is substantially of the colour red, this coming from the blood, with some regions having an orange or yellow bias. The ophthalmologist is able to use this visual image to aid in the diagnosis of the health of the eye. Thorough diagnosis requires the use of a battery of other oculometric instruments in addition to the fundus camera.

SUMMARY OF THE INVENTION

In a first aspect, there is provided a method for retinal health assessment comprising imaging the retinal fundus of a patient's eye at different wavelengths within a spectral range; determining spectral reflectivity of the retina for each pixel within a field of view (FOV); and assessing retinal health based on the spectral reflectivity of the retina.

In an embodiment, the step of imaging comprises illuminating the retinal fundus with an illuminating light energy and the step of determining spectral reflectivity comprises comparing, on pixel-by-pixel basis, the illuminating light energy with a reflected light energy.

The imaging can include capturing a sequence of substantially mono-spectral retinal images and the spectral reflectivity of the retina can be determined from an analysis of the sequence of substantially mono-spectral retinal images. The spectral reflectivity can also be determined on the basis of specular retinal reflectivity and diffuse retinal reflectivity data obtained from the imaging step.

The imaging can be through a pupil of the patient's eye and can be obtained by illuminating the retinal fundus through a central region of the pupil and detecting reflected light through an annular region surrounding the central region. The total area of the pupil can be measured and used to normalize the reflected light energy to determine the spectral reflectivity of the retina independent of the total area of the pupil. The surface topology information of various reflective layers of the retina can be obtained and used for assessing the retinal health.

In an embodiment, the retinal fundus can be illuminated using polarized light and the reflected light from the retina can be analyzed polarimetrically to determine the spectral reflectivity of the retina.

In another embodiment, a retinal auto-fluorescence factor can be determined by illuminating the retinal fundus at a first wavelength and imaging the retinal fundus at a second wavelength. The second wavelength is equal to an auto-fluorescence wavelength of the fundus. The retinal health can be assessed based on the retinal auto-fluorescence factor.

In yet another embodiment, a retinal oxygenation can be determined by measuring the spectral reflectivity of the retinal fundus at two or more predetermined wavelengths. The retinal health can be assessed based on the retinal oxygenation.

The imaging of the retinal fundus can be performed using substantially mono-spectral light emitting diode (LED) illumination sources or by using a narrowband of spectral radiation. In addition, the imaging of the retinal fundus can be obtained by illuminating the retinal fundus with substantially mono-spectral light. Preselected reflections of the substantially mono-spectral light can be blocked by placing masks along an imaging path.

In another aspect, there is provided a retinal health assessment system comprising an optical unit and a processor. The optical unit images the retinal fundus of a patient's eye at different wavelengths within a spectral range and the processor determines spectral reflectivity of the retina for each pixel within a field of view (FOV), and assesses retinal health based on the spectral reflectivity of the retina.

The system can include a cardiac sensor for coordinating the imaging of the retinal fundus with a cardiac cycle of the patient.

The system can also include a processing means for distinguishing between specular retinal reflectivity and diffuse retinal reflectivity.

In an embodiment, the system includes a plurality of illumination sources coupled to the optical unit in a rotating periscope arrangement for selective individual alignment with an illumination path of the optical unit. The illumination sources can each comprise a substantially mono-spectral LED illumination source.

In another embodiment, the system includes one or more fixation targets for fixing the patient's gaze during imaging. In addition, the system can include one or more optical masks to block preselected reflections in an imaging path of the optical unit.

In yet another embodiment, the system includes a display connected to the processor for displaying retinal health assessment data generated by the processor.

Furthermore, the system can include a position controller for adjusting a position of the optical unit during imaging for alignment with the imaging path relative to the patient's eye.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
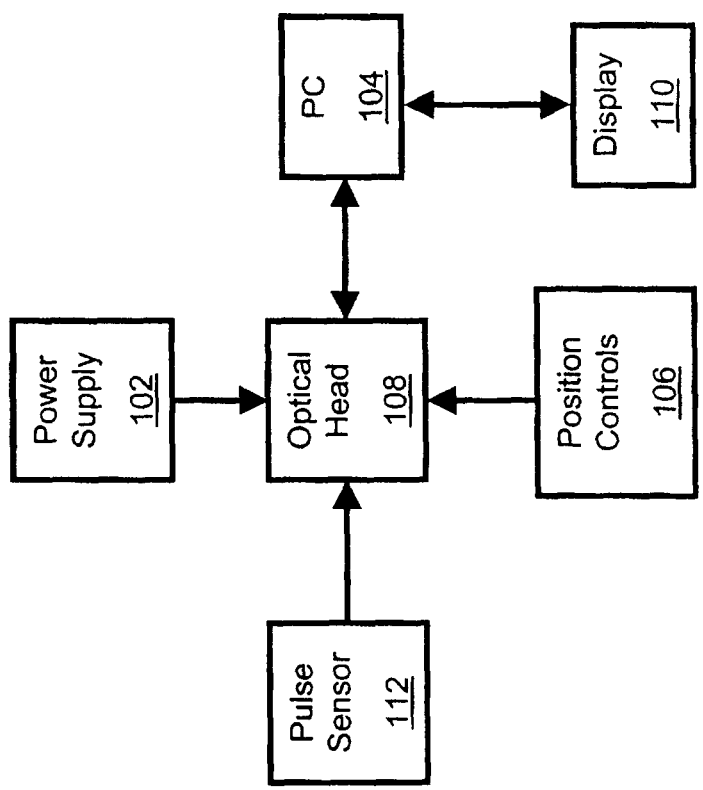
FIG. 1 is a schematic block diagram of the retinal fundus imaging system according to an embodiment.

The fundamental limitations of fundus imaging as a diagnostic tool are rooted in the subjective nature of the image evaluation and in the substantial variations in the image that result from the uncertainties of many of the parameters that are integral to the imaging process and presentation.

The color perception of the human eye is variable. No two people perceive the same colour image in the same way, and in some cases, one may suffer from a form of colour-blindness, commonly an inability to distinguish red from green. As there is only a very minor blue component in a retinal image, red-green colour blindness effectively removes all colour information. The colour perception of the human eye is also conditioned by the intensity and spectrum of the environmental lighting; the background illumination may come from daylight, some form of fluorescent lighting, or incandescent lighting.

Similarly, the color presentation of images using photographs or electronic displays is variable. Any photograph or display is limited by the gamut of colours enclosed by the specific three primary colours employed. The process and manufacturing tolerances will result in a spread from one photograph or display to another, which will be compounded by aging effects and the impact of environmental influences such as temperature.

Visual observation of the fundus is essentially a rudimentary form of multispectral imaging where the three colour channels correspond to those of the observing eye. The spectral sampling locations and widths of the three visual colour channels do not necessarily correspond with those that would be chosen in an optimal fashion determined by the reflection characteristics of the retina associated with specific retinal diseases or defects.

Potentially important information contained in small variations of the intensity or brightness of the image may be lost where the dynamic range of the display is limited; such variations may be hidden in a white-out region or a darkened region, or simply missed as the human eye is incapable of discerning intensity or brightness changes of less than a factor of two.

The limitations of the display and its perception are further compounded by the uncertainties associated with the generation of the image. The illumination source energy will vary from camera to camera, from time to time, and with age. This will result in concomitant variations in apparent image brightness. The sensitivity of the image sensor, be it film or electronic (CCD), will vary from unit to unit. This will also result in concomitant variations in apparent image brightness. The optical transmission efficiency is not always high, especially in the presence of cataracts. The efficiency will also vary across the spectrum. This will result in concomitant variations in apparent image brightness and colour. The amount of illumination that is reflected from the retina is strongly dependent on the size of the pupil. As the size of the pupil varies greatly from person to person and with environmental lighting conditions, this will result in concomitant variations in apparent image brightness.

The reflectivity of the retina is strongly dependent on the ethnicity of the person, as a consequence of the different concentrations of melanin. People of African ethnicity have higher melanin concentrations resulting in low retinal reflectivity and this causes dark retinal images that are difficult to interpret.

Ophthalmologists need to carefully track the progression of the retinal health problems of their patients in order to prescribe the most appropriate course of treatment. For this purpose, they carry out examinations over time to establish longitudinal trends. However, because of the variations and uncertainties listed above, the utility of fundus cameras for longitudinal monitoring is severely limited.

Generally, the present invention provides a method and apparatus for quantitative imaging the retinal fundus. The method for retinal health assessment comprises imaging the retinal fundus of a patient's eye at different wavelengths within a spectral range and determining spectral reflectivity of the retina for each pixel within a field of view (FOV). The retinal health is assessed based on the spectral reflectivity of the retina.

The retinal fundus is illuminated with an illuminating light energy and the spectral reflectivity is determined based on a comparison, on pixel-by-pixel basis, the illuminating light energy with a reflected light energy. Thus, each and every point on the retinal fundus image equal to the area of the pixel can be individually monitored and analyzed for obtaining a retinal health assessment. Information about retinal health previously unavailable can be obtained from the enhanced pixel-by-pixel evaluation of the image data.

The quantitative fundus surveillance instrument, according to an embodiment, generates spectral reflectivity data based upon the capture and analysis of a sequence of substantially mono-spectral retinal images. The electromagnetic spectrum within which these images may be captured can extend over the entire ocularly transparent spectral region that includes the visible spectrum and infrared spectrum (i.e., between 400 and 1400 nm).

The image data obtained with an embodiment of the instrument is calibrated in terms of diffuse retinal reflectivity and the specular retinal reflectivity. The diffuse or scattered reflection from the retina is well modeled by that of a Lambertian surface where the reflected light is directed over an entire hemisphere according to the cosine law of distribution. The ratio of diffusely reflected light energy to incident light energy is governed by the surface reflectivity, a dimensionless quantity with a value that lies between zero and one. The retinal reflectivity is a function of wavelength and other factors, and generally lies in the region between 0.001 and 0.02, the former being typical at the shortest (blue) wavelength and the latter occurring at infrared wavelengths for eyes with low melanin content.

The reflection of light from the retina is not entirely of a diffuse character. A small portion of the incident light is reflected in a specular or mirror-like fashion. The specular or mirror-like reflectivity indicates the flatness of the surface and tends to be relatively independent of wavelength. Unless this is factored into calculations following measurements, this would introduce small errors in the estimation of the diffuse reflectivity. The instrument, according to an embodiment, includes a measurement means to distinguish between the two modes of reflection.

The diffuse spectral reflectivity is characteristic of the chemical composition of the organic tissue just behind the retinal surface. While the spectral reflectivity profile is indicative of certain health conditions applying to vision, it is also indicative of other health conditions such as diabetes. The eye functions as a window to the blood and thus enables non-invasive blood analysis. It may therefore be appreciated that the instrument, according to an embodiment, includes capabilities beyond those that are strictly of interest to ophthalmologists.

Conversely, the specular reflectivity is substantially independent of the chemical composition behind the retinal surface and is substantially constant over the spectrum. Measurement of the specularly reflected light can be used to estimate the spectral absorption within the ocular lens and the aqueous and vitreous humours (intra-ocular transmission losses) and parameters that are also of medical interest, and that would normally contribute uncertainty to the diffuse reflectivity measurement. The spectral absorption can be also factored into calculations following measurements, to avoid the introduction of errors in the estimation of the diffuse reflectivity.

Knowledge of the level of absorption is also independently valuable to the ophthalmologist as it is indicative of certain health problems such as the presence of cataracts.

The measurement of retinal reflectivity is not the only non-invasive measurement operation that can be implemented by an embodiment of the instrument. The retina has the property of auto-fluorescence whereby it absorbs light at one wavelength and simultaneously emits light at a longer wavelength. The strength of the auto-fluorescence is governed by the presence and concentration of lipofuscin and drusens, both of which are indicative of ocular health conditions. The instrument, according to an embodiment, has the capability to illuminate the retina at one wavelength while capturing the retinal image being emitted at another, for example, longer, wavelengths. The image data is calibrated in terms of the retinal auto-fluorescence factor, a dimensionless quantity analogous to reflectivity but generally having a much lower value.

In summary, the embodiments of the instrument are capable of several types of measurement, including mapping retinal spectral reflectivity, measuring interior specular absorption, and mapping retinal auto-fluorescence, employing retinal illumination having wavelengths anywhere between 400 and 1400 nm. In this way, it has greater value to the ophthalmologist who would otherwise have to invest in additional instruments, if available, and devote more time to the patients.

Retinal Diffuse Reflectivity Measurement

The relationship between the photoelectron count N per pixel and illumination source energy E (expressed in photons) reaching the cornea is given by:

$$N = \eta A E T U \tau^2 r / (M \pi s^2)$$ Eqn. (1);

where $\eta$ is the quantum conversion efficiency of the image sensor; A is the pupil area; r is the retinal diffuse reflectivity; $\tau$ is the one-way transmission through the eye; s is a dimensional parameter of the eye; T is the transmission through the image viewing optical path; U is a uniformity factor applying to the illumination field; and, M is the ratio between the illumination field solid angle and the pixel field solid angle.

The reflectivity is calculated from Eqn. (1), where the measured variables are N, E, A and $\tau$ while the other parameters are known.

Typically, conventional fundus cameras, produce colour images that are displayed either on a screen or printed and then presented to a professional physician ophthalmologist for a subjective qualitative assessment.

The instrument, in an embodiment, generates objective quantitative data for every pixel in addition to being able to generate images. The numerical data for each pixel presents an approximation to the absolute retinal reflectivity (or fluorescence coefficient) at the sampling wavelength. This can be calculated because the instrument not only counts the photoelectrons received in each pixel, but also measures the total amount of energy launched and the diameter of the pupil. Thus, the total area of the pupil can be measured and used to normalize the reflected light energy to determine the spectral reflectivity of the retina independent of the total area of the pupil. The surface topology information of various reflective layers of the retina can be obtained and used for assessing the retinal health. This level of absolute measurement enables more information and greater reliability of assessment to be obtained. The total launched energy is measured using an internal energy monitor, while the pupil diameter is measured when the image of the cornea is captured when alignment is complete.

Estimation of Retinal Oxygenation

In addition to measuring the retinal reflectivity or fluorescence coefficient, an embodiment of the instrument can measure retinal oxygenation. Retinal oxygenation is typically assessed by measuring the reflectivity at two or more carefully chosen wavelengths. These wavelengths have been located in the visible region compatible with that of conventional instruments that are restricted to making measurements at one location, or to making measurements only of arterioles and venules.

Using the quantitative measurement capabilities of an embodiment of the instrument, oxygenation estimates for the full retinal area can be obtained. This is achieved using at least four models each addressing a different region, specifically the optic nerve, the fovea, arterioles/venules, and the remaining area—the majority.

Unlike conventional instruments that measure using very narrowband source such as lasers, or slightly wider band rectangular spectrum sources created using optical band-pass filters, an embodiment of the instrument uses Light Emitting Diodes (LED) with relatively broad Gaussian spectra.

In an exemplary embodiment, the sources located near 505 nm, 617 nm and 850 nm are chosen. This is a unique permutation. The rationale is that the 505 nm measurement gives a result substantially independent of oxygenation or pigmentation, the 617 nm measurement gives a result strongly dependent on oxygenation but also influenced by pigmentation, while the 850 nm measurement gives a result strongly influenced by pigmentation and also influenced by oxygenation. Combining these enables one to substantially eliminate the pigmentation factor and determine the oxygenation level.

Quality of Retinal Imaging

The quality of the diffuse retinal image can be described in terms of three resolution terms, viz. the spatial resolution; spectral resolution; and, the reflectivity resolution.

The spatial resolution is determined by the combination of the pixel count of the image sensor, normally a CCD, the field-of-view (FOV) on the retina, and the limitations of the eye itself. Good spatial resolution is desirable, as is a large FOV that includes both the central macular region and the optic nerve region. For example, if a FOV of 40 degrees is stipulated and imaging performance is close to being diffraction limited, the required pixel count is in the region of four million.

The use of a panchromatic CCD and sequential monochromatic imaging at different wavelengths ensures that the full spatial resolution is available at each and every wavelength. This contrasts with the use of a conventional colour CCD where the Bayer mask pattern allows only half of the pixels to be allocated to the green channel and only a quarter of the pixels to each of the other two channels blue and red. It also ensures that none of the illuminating energy is wasted. To achieve a similar spatial resolution with a conventional colour CCD, the retinal pulse illumination energy would have to be increased by a factor of four. While in principle, it is feasible to increase the illumination energy, in practice this is subject to safety limits and considerations of patient comfort. Moreover, there are limits to the ability of any illumination source to increase the energy in each illumination pulse and these may be dominant.

Another source of loss of spatial resolution is the blur that results from microsaccadic activity of the eye while it is nominally fixated. To keep this within acceptable limits, the duration of the retinal illumination pulse must be kept low, typically to the order of a few milliseconds.

The spectral resolution requirements are determined by the spectral reflectivity profile of the retina. There is no apparent line structure to the retinal reflection spectrum and the rate of variation with wavelength is low, with complete reversal cycles typically occupying spectral widths of the order of several tens of nanometers. For this reason the spectral resolution requirements are generally compatible with the use of substantially mono-spectral LED illumination sources and do not require the use of narrowband laser sources.

The reflectivity resolution or uncertainty is determined by the number of photons captured per pixel at the image sensor in association with the quantum conversion efficiency of the sensor. As may be expected, the more photons received per pixel, the better quality is the image. It is, therefore, desirable to use an efficient sensor and efficient optical systems both for launching the illumination pulse and for extracting the image reflection.

Conventional colour fundus imagers require a single illumination energy pulse to simultaneously supply the needs of three wavelength channels. In requiring only sufficient energy per pulse to address the reflectivity resolution needs of one substantially mono-spectral channel at a time, an embodiment of the instrument enables the number of photons per pixel to be sufficient while keeping the retinal illumination at a relatively low and comfortable level.

It may be appreciated that the use of substantially monospectral sequential imaging, for the same spatial and reflectivity resolution requirements, reduces the required retinal illumination pulse energy by a factor of 4×3 or 12 from that of a conventional colour fundus imager, greatly adding to patient comfort. Alternatively, this advantage can be apportioned between reduced pulse energy, and better spatial and reflectivity resolutions.

In addition to the uncertainty in reflectivity contributed by the finite number of photons per pixel in the image, there are potential uncertainties caused by various other elements in the overall system. These elements must all, therefore, be monitored and the results factored into the reflectivity calculations and are now described.

The illumination pulse energy: In an embodiment, a portion of the pulse energy is diverted to a monitor sensor. The measurement from the monitor is applied to the calculation of reflectivity to compensate for any factor such as ageing that could cause the pulse energy to change.

The pupil size: The amount of energy collected from the retina is directly proportional to the pupil area. In an embodiment, the pupil image is captured and used to calculate the area. This in turn is factored into the reflectivity calculation.

The eye transmission: Light that is collected from the retina passes through the eye twice, first on its way in and then on its way back out. Any absorption along the transmission path within the eyeball needs to be factored into the calculation of the reflectivity. As described above, the ability of the instrument, according to an embodiment, to discriminate between specular and diffuse reflections enables an estimate of eye transmission to be made that can be used to calculate the absorption correction.

The instrument optical path and sensor efficiencies: These can be determined by calibration during manufacture and are normally stable over time.

Non-uniformity in the illumination field: This can also be measured and calibrated during manufacture.

Reflectivity changes induced by the cardiac pulse: It is known that the reflectivity of the retina at some wavelengths varies with the instantaneous blood pressure and is, therefore, cyclic and synchronous with the cardiac pulse. In an embodiment, the cardiac pulse is monitored by a sensor and the result is used to synchronize the image capture with the cardiac pulse, thus removing any random variation that would occur if the image capture moment was at a random point of the cardiac cycle. Consequently, image capture events are typically spaced at intervals of one second.

Illumination Arrangements

Conventional instruments illuminate with broadband white light. In order to obtain a good image by avoiding chromatic aberration, the overall imaging optics including the human eye itself must be highly achromatic. This is not easy to achieve, especially over a wide spectral range. As a result, the image is normally optimized for one wavelength, typically green, and deteriorates at other wavelengths.

An embodiment of the instrument captures multiple images using only a narrowband of spectral radiation at a time. For each spectrum used, the camera position is automatically optimized to provide the best resolution, from blue through to infrared over a substantially 2:1 ratio of wavelength. This enables the generation of high-resolution images anywhere within the overall instrument measurement spectral range.

As indicated above, the preferred means of illumination is the LED. LEDs can be pulsed for a short duration and are robust and reliable with consistent output that is repeatable. The preferred type of LED is surface emitting as distinct from edge emitting. A typical source size of a type suitable for this application is about 1 millimeter. As the drive current is likely of the order of an ampere, it is advisable to control the rate of the rising and falling drive current edges to prevent unwanted electromagnetic emissions at radio frequencies.

The light from the LED can be collected by a condenser lens and then relayed into the pupil through an optical path that will generally contain lenses, mirrors and beam splitters. The ray bundle or optical mode-volume from the LED is limited using apertures such that, where it reaches the cornea, it has a prescribed area and convergence. Typically, the ray bundle will have a diameter of 1 mm at the cornea and will launch in the region of 50 to 100 micro joules of energy with a single pulse.

In order to obtain proper illumination, the form of the illumination spot has to be determined. The illumination spot has a defined beam diameter at the corneal surface, typically 1 mm, and a defined cone angle of convergence suitable for illumination a sufficient portion of the retina. This could be 50 degrees. In an embodiment, the illumination beam is formed from the source LED by two circular apertures used in association with a series of lens elements. One aperture defines the spot diameter and the other aperture defines the cone angle.

The multispectral fundus mapper, in an embodiment, employs a multiplicity of LEDs each having a different optical spectrum. These are coupled into the illumination path sequentially in time. There are several options for efficiently coupling the sources to the common illumination path. One option is to employ a multiplicity of optical beam combiners that are spectrally discriminating. However this approach is complex where there are many sources and each beam splitter contributes loss. Every source requires a beam combiner matched to its spectrum, such that it passes the one spectrum while reflecting all the others. Moreover, it is inflexible inasmuch if a source with a new spectral region is introduced, a beam splitter matched to this requirement would be needed.

Another technique is to mount the various illumination sources on along a circular locus on a mount that can rotate, enabling the selected source to be placed in the correct position, one at a time. This arrangement suffers from the fact that each source is electrically connected with wires and all these wires would be constantly flexing as the selected source changes, resulting in eventual fatigue and failure. Moreover, there would be limits as to the direction of motion, as an indefinite movement in one direction would cause the wires to twist together.

Yet another technique would be the same as above but using electrical slip rings to connect the electrical power. However, such slip rings are not commodity items and would be subject to corrosion and degradation.

Some form of switching or multiplexing is needed to accommodate several LEDs that are to be activated in a sequence. Spatial multiplexing is inherently inefficient and therefore unsuitable. Passive wavelength multiplexing is more efficient but is difficult to arrange when operating with large mode volumes. It is also inflexible in that the multiplexing filters must be designed to be compatible with the specific LED wavelengths.

In an embodiment, the instrument employs an active switching arrangement that consists of a rotating periscope. The periscope is located in the collimated space following the first condenser lens. The periscope is highly efficient and is suitable for all combinations of source wavelengths and can be operated by a stepper motor. The LEDs are all deployed on a circular path. An advantageous feature of the rotating periscope over potential alternative active arrangements is that there is no requirement for the source LEDs to move and consequently no constant stressing of wire harnesses that would result in fatigue and failure. There is also no limit to the sequence combinations that can be used.

In an embodiment, the illumination sources are coupled one at a time to the common illumination path using a rotating periscopic arrangement. The LEDs are, as described before, mounted along a circular locus and are stationary while the periscope is moved. This provides a highly efficient coupling and is totally achromatic—that works well with any combination of source spectra. Moreover, there is total flexibility of movement direction and sequences.

Each LED source is mounted next to a dedicated aspheric condenser lens that collects a proportion of the total LED power and collimates it. The collimated light passes through an aperture that defines the cone angle associated with the illuminated corneal spot. The collimated beam then passes through the periscope. On the other side of the periscope, a second lens focuses the light upon an aperture that defines the spot size.

In an embodiment, one LED emitting in the infrared part of the spectrum is used for focusing purposes and be seen by the patient. This LED is associated with a cross shaped mask in the collimated space following the condenser lens. This cross shape is projected on to the retina and provides a high contrast image that eases the task of accurate focusing.

The selection of the LEDs by wavelength is driven by the measurement requirements. Commonly, one of the requirements is the simulation of a conventional fundus colour image. This requires that the LED set include a blue, a red and a green LED. In order for the measurement of retinal oxygenation, the use of an infrared LED, a red LED (the same as above), and a cyan LED has been found suitable.

For fluorescence purposes, a blue LED is required, possibly supplemented by a LED at a different wavelength. It is necessary to apply an optical filter to the light from a LED to be used for stimulating fluorescence. This filter substantially passes the LED light but effectively blocks the long wavelength skirt of the spectrum that can stretch out considerably albeit at a low level. This filter can also be deployed in the collimated space following the condenser lens.

It may be appreciated that the images obtained using one LED may be able to serve several purposes, and so avoiding the need for a large number of LEDs. For most purposes, it appears that the use of 5 or 6 LEDs will be sufficient. In practice, these needs can be met using commercially available LEDs; however, it is conceivable that a special LED may need to be developed for some special application.

The use of a laser may be feasible in place of a LED in certain circumstances. However, care will be needed to avoid coherent interference effects that increase the uncertainty of the measurements; to manage the power to ensure patient safety; and to assure a sufficiently even distribution of energy over the illumination field. This latter requirement may call for the use of a diffusing element to convert the laser light from being in a single spatial mode to being in multiple spatial modes similar to those of a LED.

Imaging Arrangements

The imaging system that relays the reflected light from the eye to the image sensor is an important part of the design of any retinal imaging system. In addition to faithfully rendering the image with maximum resolution and minimum distortion over a wide range of wavelengths and a wide range of eyes (from those with myopia to presbyopia), the relay system of an embodiment the instrument includes places to deploy masks and filters, some on a dynamic basis.

In an embodiment, the image relay design is substantially achromatic when used in conjunction with a standard human eye that has substantial chromatic aberration. The position of the image sensor is controlled by a precision motorized drive that allows fine-tuning to automatically optimize the focus for each wavelength.

The same motorized drive is used to automatically set the focus to accommodate the prescription of the patient. The final focus is achieved by manual control of the motorized drive, with the operator using a visual presentation of the retinal image in the infrared region.

At one point, a filter can be inserted for use with auto-fluorescence measurements. This filter blocks the reflected light at the exciting wavelength, e.g. blue, but passes efficiently the excited light in the longer wavelength spectral region.

At another point, a mask can be inserted to alter the distribution of the image between its specular and diffuse components.

A technical challenge in any fundus imager design is to accommodate the very large ratio between the illuminating source power and the power that is collected by the image sensor. This ratio is of the order of a million to one. The threat is that the magnitude of any unwanted reflection could easily swamp and wash out the wanted imaging power from the retina. The main sources of such unwanted reflections are a) the corneal reflection, b) reflections from any optical elements (lenses and windows) in the common optical path shared by the illuminating and reflected light, and c) any polymer intra-ocular lens (IOL) typically inserted after cataract surgery.

Typically the common optical path includes just one lens doublet in addition to the corneal surface that reflects typically about 3% of the incoming power. As the retina reflects back through the pupil only about 0.1% of the incoming power, it is evident that the corneal reflection is typically 30 times greater unless measures are taken to avoid or remove it. The lens doublet reflections are less as the doublet surfaces are given broadband antireflection coatings that limit the two reflections to less than 1% each; however, this is still much greater than the retinal reflection power.

In the prior art, the usual technique employed is to spatially segregate the corneal area of illumination from the corneal area of collection. Typically, the illumination is in the form of an annulus while the collection is taken from the circular area in the centre of the annulus. The corneal reflection then is reflected outwards and avoids the central area wherein the collected power travels. The converse arrangement may also be used, where the illumination is in the centre and the collection made through the annulus.

A difficulty with the annular illumination technique is that the annulus can easily approach the border of the pupil, which risks illuminating the edge of the iris, causing a large reflection. Therefore, the size of the annulus must leave a margin to avoid the large reflection resulting in a relatively small area for collection. Hence, to obtain sufficient light to obtain a good image, the eye pupil must be dilated (mydriated) or a large illumination level must be used; in either case the patient experience is negative. A further difficulty with annular illumination is the loss of efficiency that generally results from having to transform the illumination source shape into the annular illumination shape.

If the converse arrangement is used, although the illumination arrangements are relatively simple, it is more difficult to obtain and sustain the required quality of imaging when collecting from the annular field. Moreover, any optical defects of the eye itself become more limiting when operating with the larger diameter.

Another version of the prior art separates the unwanted reflections using a polarization technique. The incident light is polarized and the light specularly reflected from the cornea is similarly polarized. The diffusely scattered light reflected from the retina is largely unpolarized. Therefore, the collected light path is equipped with a polarizer that blocks the light having the same polarization as the incident light, leaving only the light from the retina. However, the eye also has some polarizing characteristics that degrade the value of this approach. As a matter of practicality, it is also difficulty to obtain polarizers that operate well over a large spectral range.

As discussed earlier, in conventional fundus camera, the retinal illumination system and the retinal image collection system are integrated. The two optical systems are usually combined with a beamsplitter angled at 45 degrees to one of the paths.

Conventionally, the beamsplitter is located at a plane in the optical system that is a conjugate image plane to the corneal surface. Moreover the beamsplitter usually consists of a mirror with a small circular hole in the centre. The illumination path reflects off the mirror into the eye, while the retinal image path is directed through the hole in the centre.

The conventional arrangement was pioneered by Helmholtz in the 19th century and has remained substantially unchanged ever since. Its prime virtue is that it effectively removes from the retinal image path the reflection from the corneal surface; this reflection is typically about 3% of the incident light power and would otherwise dominate and substantially degrade the quality of the retinal image that is at a very much lower power level.

The conventional form of arrangement results in the illumination beam at the corneal surface having an annular shape, with a diameter of about 3 mm. The retinal image path passes through the hole in the centre of the annulus. The size of the illumination beam at the pupil is small enough to fit within the pupil, but allows sufficient area within the central circle to enable sufficient power to be collected from the retina.

The retinal image is made up of reflections that occur at various locations and depths within the retina. Part of the image is contributed by diffuse reflections resulting from multiple scattering events within the tissue, while part is specularly reflected from discrete layer interfaces characterized by small changes in refractive index.

The diffuse reflections are generally evenly spread out in a polar distribution that is approximated by the Lambertian model. In contrast, the specular reflections, being mirror-like, are directed such that the angles of incidence to the reflection surface are equal to the angles of reflection, and the resulting direction is dependent upon both the incident angle and the gradient angle of the retinal surface. While the retinal surface is spherical to a first approximation, it has a texture and detailed contour that is characteristic of the proximate structural elements such as the vasculature and any deformations that may be natural or characteristic of a pathology.

In the conventional fundus camera, the incident angles of the rays illuminating the retinal surfaces are smoothly distributed over a range that is determined by the size of the illuminating annulus at the ocular lens just behind the cornea and the effective focal distance from the ocular lens to the retina. This translates into a range of about plus and minus four degrees. The collection angle in the centre is about one to two degrees in diameter.

If the retinal surface is perfectly smooth and normal to the collection axis, no specularly reflected light from the surface will be collected. If however, the retinal surface gradient is angled from the normal to the collection axis, some of the specularly reflected light may be collected, depending on the surface gradient angle. Because the incident light is distributed over a range of angles, the amount of collected light from each retinal pixel will be only weakly dependent on the retinal surface gradient.

In order to overcome limitations of the conventional imaging system, it is proposed that the illumination and collection paths be transposed. This results in the illumination at the cornea being in a central circular area with the retinal image being collected through the surrounding annular area. As a consequence, all the light reaching the retinal surface pixel arrives from substantially the same direction; it is not dispersed over a range of angles. All the light specularly reflected from a retinal surface pixel is directed in the same direction and is not dispersed over a range of angles.

Depending on the direction of the reflected light, it will then either be substantially collected through the viewing annulus or it will substantially not be collected; a small change of incident angle can result in a large change in the amount of collected light. The amount of specular collected light from each retinal pixel will be strongly dependent on the retinal surface gradient.

The overall result is that the retinal image resulting from this arrangement will include a specular component that includes the gradient contours of the retina, features that are normally dispersed (smeared) and substantially not discernable with the conventional fundus camera design, thus providing a substantial advantage over conventional fundus cameras.

Furthermore, in order to further improve non-surface effects, the light launched into the eye can be polarized and the light reflected from the retina can be analyzed polarimetrically such that the portion of the reflected light that is orthogonally polarized with respect to the illumination is collected. This substantially blocks light that is specularly reflected—corresponding to light reflected from the surfaces as distinct from being backscattered just below the surfaces. In an embodiment, the incident light is linearly polarized and the reflected light passes through a similar polarizer at right angles. More generically, light with any polarization state can be used for. Preferably, to minimize the impact of any birefringence within the eye that will have preferred orientations, circularly polarized light can be used for illumination and light having circular polarization of the opposite sense can be collected.

Typically, the diffusivity is spectrally dependent and is indicative of the chemical content. However, the specular component is also spectrally dependent, but not through the reflective action but instead through the intermediate absorption. Overall, the reflection model of the retina is a complex aggregation of spectrally dependent reflective and absorptive layers.

Clearly, the ability to analyze the retinal reflections in terms of specularity and diffusivity as well as magnitude and spectrum adds further to the diagnostic potential of the retinal fundus imaging system described herein.

In an embodiment, the illumination is in the form of a small circular area in the centre and the collection is taken from the surrounding annulus. Illumination using a small circular area in the center enables an efficient match to the illumination source, in this case an LED, and provides maximal margin from reflection interference with the iris. Collection from the annulus provides a good level of collected power. Means for blocking the unwanted reflections and means for maintaining high image quality are employed when collecting from the off-axis annular field as described below.

The separation or blocking of the unwanted light reflected from the central areas of the cornea and the nearby objective lens is achieved by the use of masks of a suitable size and location being placed in the optical collection path prior to the image sensor. Every surface generating an unwanted reflection requires a mask. These masks will block all the unwanted reflections but will block only a small proportion of the wanted reflections from the retina. The basic principle used here is that the intermediate virtual image planes associated with the retina, the cornea and the objective lens surfaces, occur at different locations and that the real images of the unwanted reflections are small in relation to the area occupied by the wanted light at those locations.

Miscellaneous Aspects

In addition to the details provided above, a number of supplementary features can be included in various embodiments of the instrument.

In an embodiment, there is provided a means to correctly align the optical head to the eye of the patient. The patient rests his/her chin on a chin-rest and presses his/her forehead against a forehead brace. These two measures stabilize the patient. Typically, a view of the cornea is then displayed to the operator, who can then control the lateral and vertical positions to centre the instrument.

In another embodiment, there is provided a means to accurately set up the optical head at the correct working distance from the patient, typically in the region of 20 or 30 mm. At the optical port facing the patient, the illuminating light converges to a small spot that is coincident with the corneal surface. The working distance for this is fixed, for example at 20 mm. To assist the operator achieve this setting rapidly and accurately, a live view of the cornea is presented to the operator, initially for lateral alignment purposes. The cornea is illuminated by two LEDs emitting in the invisible infrared part of the spectrum, one either side of the objective lens and having the two beams incident at about 45 degrees to the face. The operator sees a reflection of these two LED sources on the corneal surface. When the working distance is correct, the size of these reflected images is minimized to two small spots coincident with the corneal surface. At any other distance they appear as annuli where the diameters increase with the distance. If the wrong distance is set, the illuminating light will either be diverging (too far) or will not have converged enough (too near) with the result that the illumination will deploy on the iris rather than disappear through the pupil. Alternatively, the operator can choose to focus upon the patient's iris to determine the working distance.

In addition, focusing on the retina can be achieved by longitudinally adjusting the image sensor location. In an embodiment, the first approximation to the correct position is carried out automatically where the patient prescription in terms of short or long sightedness is known.

In yet another embodiment, there is provided a fixation target or several targets upon which the patient must fixate his/her gaze during the measurement session. The light from the fixation target screen is adjustable as this affects the pupil size. During the instants of image capture, the fixation target screen is momentarily disabled to prevent light from it interfering with the retinal images.

It is inevitable that a certain amount of illuminating light finds its way to the image sensor through paths other than the retina or the prime reflecting surfaces outlined further above. As a result, there is a low level image present even when no eye is present. However, this image is consistent and can be stored and subtracted during the image-processing phase. In this way, it does not impact the accuracy of the reflectivity measurement.

Furthermore, the major unwanted reflections can be removed by deployment of suitable masks. However there remains a large multiplicity of multiple reflections between the many optical surfaces that result in a low level but finite field of unwanted light at the image sensor, typically having a quasi-Gaussian spatial profile. In an embodiment, this profile is recorded during calibration and subtracted from the images captured during normal operation. The profile varies slightly with wavelength and with camera position and these factors can be taken into account before the subtraction operation.

Based on the foregoing discussion, a description of an exemplary embodiment of the instrument is provided below.

FIG. 1 shows a high level partitioning of the system elements. These comprise, for example, the optical unit/head 108, a personal computer 104, and power supplies 102. The optical unit/head is provided with a touch screen display 110 that is used both for operator control and also for the display of images used for alignment and focusing. Attached to the optical head is a small device that straps around a finger and is used to monitor the cardiac pulse 112. At the base of the optical unit/head are manual controls 106 used to position the optical head in the three dimensions with respect to the eye under observation. Adjacent to the objective lens is the fixture that combines the chinrest and the forehead brace.

Figure 2B:
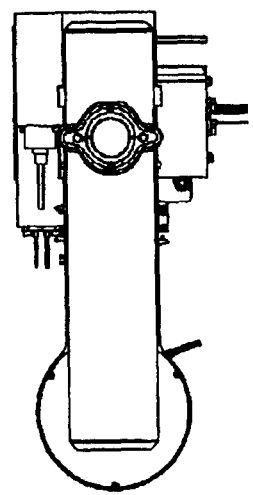
FIGS. 2A and 2B are a side elevation and a top view, respectively, of the retinal fundus imaging system according to an embodiment.
Figure 2A:
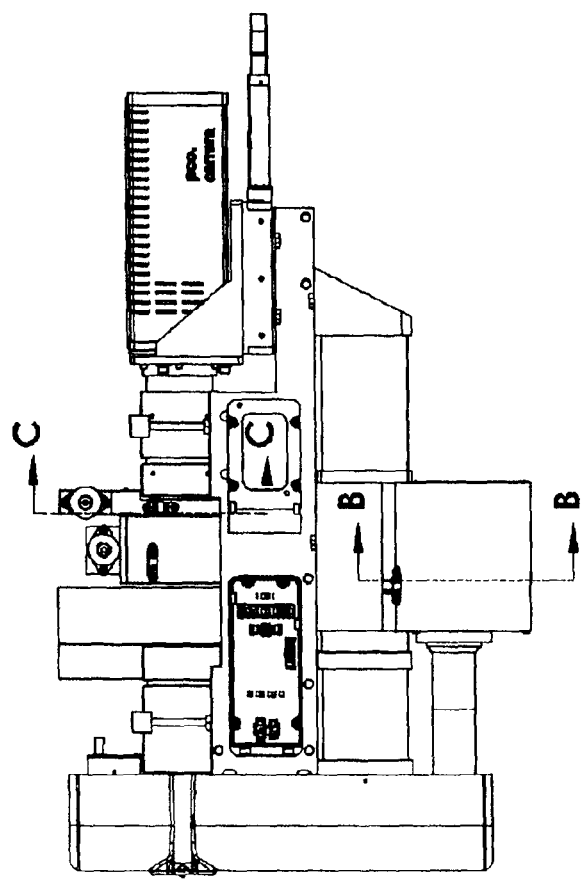
Figure 3:
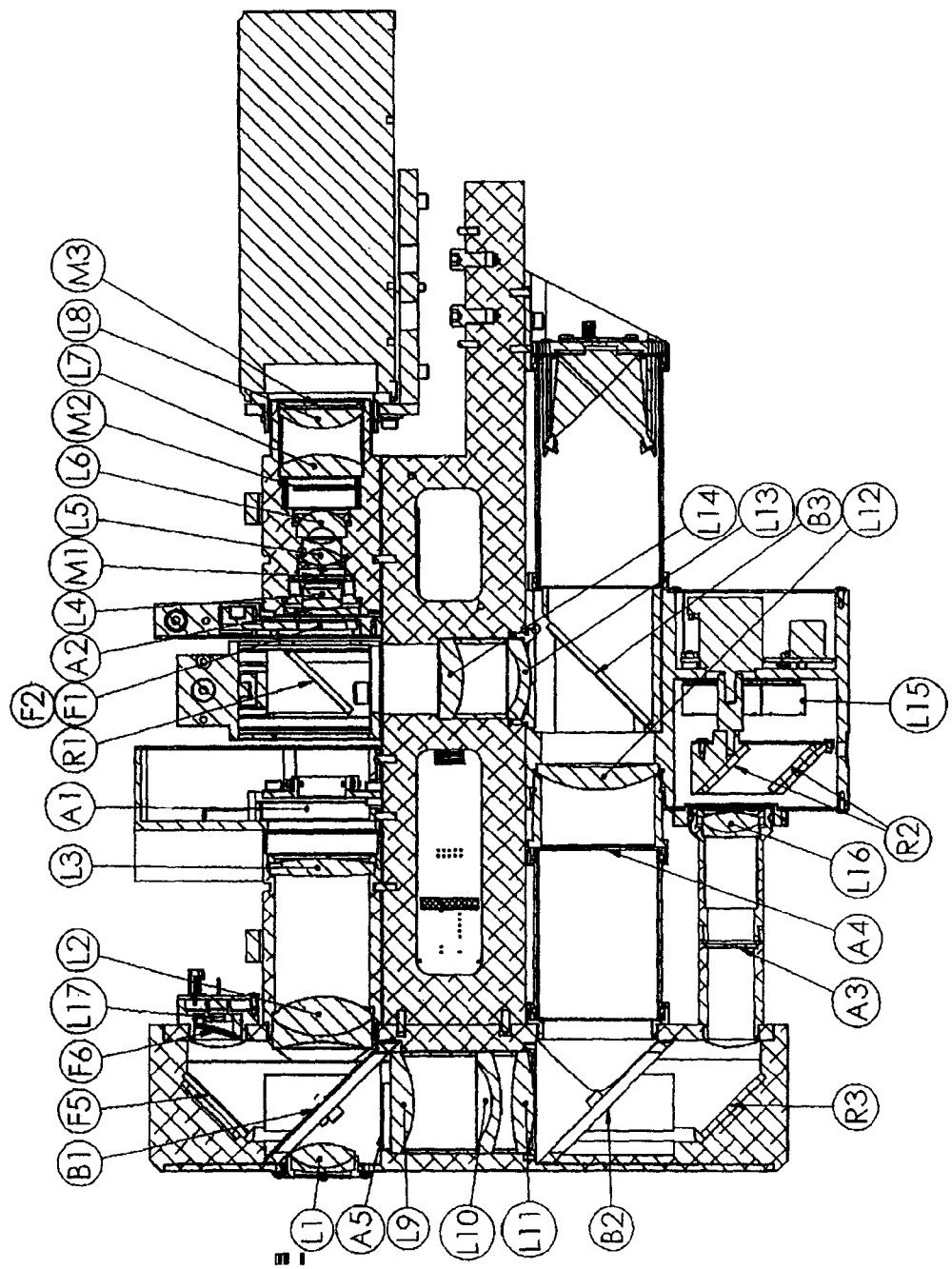
FIG. 3 is a longitudinal cross-section of FIG. 2A.
Figure 4B:
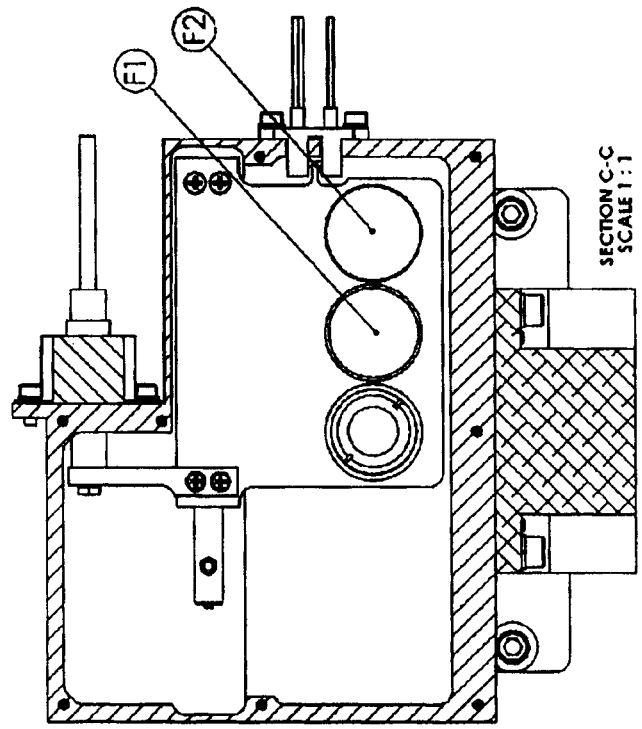
FIG. 4B is a cross-section along C-C of FIG. 2A.
Figure 4A:
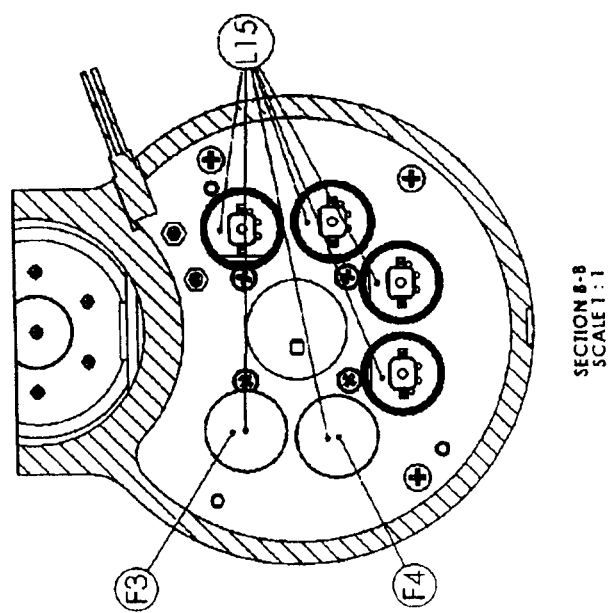
FIG. 4A is a cross-section along B-B of FIG. 2A illustrating the optical head the retinal fundus imaging system according to an embodiment.

FIGS. 2A and 2B are a side elevation and a top view, respectively, of an embodiment of the retinal fundus imaging system. FIG. 3 is a longitudinal cross-section of FIG. 2A. FIGS. 4A and 4B are cross-sections along lines B-B and C-C of FIG. 2A. FIG. 4A shows details of the optical head of an embodiment of the retinal fundus imaging system. The optical head design comprises six integrated optical systems. These consist of the retinal illumination system, the corneal illumination system, the retinal illumination pulse energy monitor system, the retinal viewing system, the corneal viewing system and the fixation target screen system. These are described below.

The Retinal Illumination System

Six LEDs are mounted on a circular locus on a printed circuit board adjacent to the lenses L15. The LEDs emit at wavelengths of 470 nm, 505 nm, 530 nm, 617 nm and 850 nm. There are two LEDs that emit at the 850 nm wavelength; one is used for focusing and is operated in a continuous rather than a pulsed mode. Suitable LED devices are made by Philips Lumileds Inc. and Osram GmbH.

Figure 5:
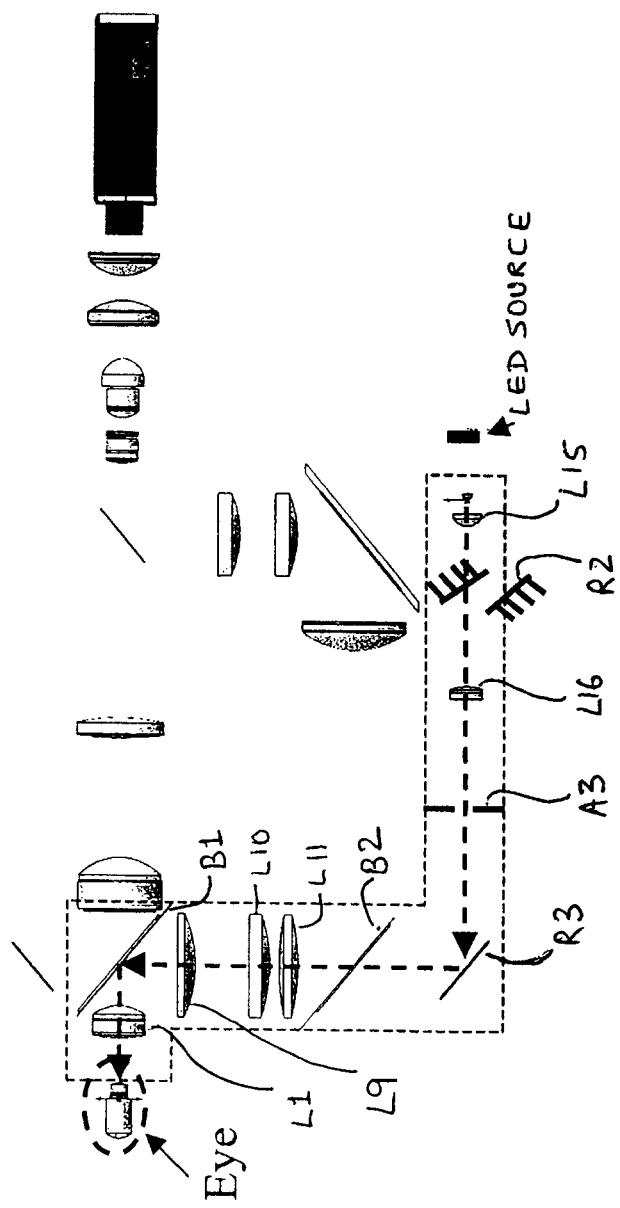
FIG. 5 is an illustration of the optical path during retinal illumination according to an embodiment.

The retinal illumination system is shown in FIG. 5. Each LED is adjacent to an aspheric condenser lens L15 set at a distance that best collimates the light from the LED. Adjacent to the lens, where appropriate, an optical filter is used to modify the LED spectrum or a projection mask is used as an aid to focusing.

The collimated light from the lens L15 is then directed to the two periscope mirror reflectors R2 that displace the beam from the offset LED axis to the central axis.

The light exiting the periscope is then passed through the lens L16 that focuses it back to create a real image at a plane occupied by the aperture A3. The image magnification from the LED to the real image is 3.33. The aperture A3 defines the size and shape of the illuminating light that will eventually reach the cornea. It is substantially filled by the real image.

After passing through the aperture, the light is reflected from R3 to travel upwards in a vertical direction. It then passes through a beam splitter B2 with low loss. The beam splitter is not used for the illumination function. The light then passes through three relay lenses, the biconvex L11, the convex-concave L10 and the plano-convex L9. At the exit of L9 is an aperture that sets the illuminating field angle.

The light then impinges upon the main beam splitter B1 where it is divided into two parts of approximately equal power. The reflected part then passes through the objective lens L1 and then converges to form the corneal spot of diameter about 1 mm.

The Corneal Illumination System

The corneal illumination system is used for alignment purposes and also to enable the size of the pupil to be captured. It consists of two infrared LEDs that are powered continuously. Each LED emits at a wavelength of 850 nm and is contained in a standard 5 mm collimating package generating a beam divergence of 44 degrees. Each LED is mounted beside L1, one on each side, and each is angled such that the centre of the projected beam is coincident with the centre of the cornea. The corneal illumination is extinguished during retinal imaging operations.

The Retinal Illumination Pulse Energy Monitor System

Figure 6:
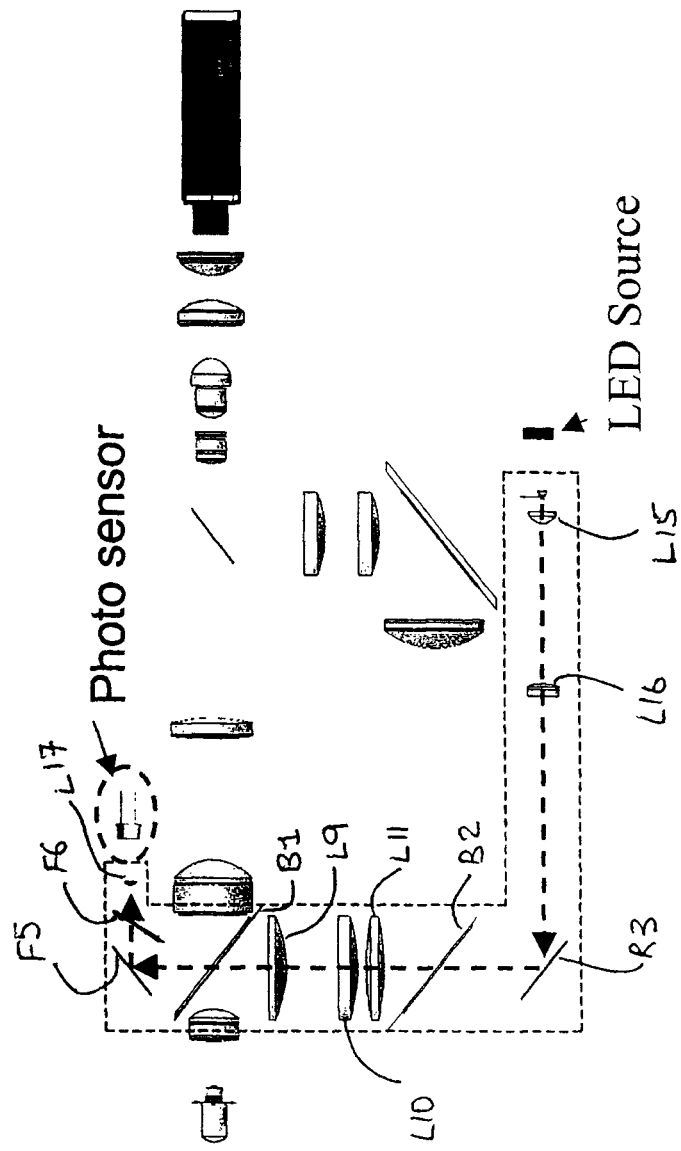
FIG. 6 is an illustration of the optical path during power monitoring according to an embodiment.

As shown in FIG. 6, the optical path from the LED to the main beam splitter B1 is the same as that described for the retinal illuminator. The light destined for the energy monitor passes through the beam splitter and proceeds to the attenuating reflector F5. This absorbs about 95% of the incident power and reflects the remainder horizontally. The reflected light then passes through a 10 dB attenuator F6 angled to the beam such as to direct any reflections to the side of the chamber where they are absorbed. The attenuated light passing through F6 then passes through the biconvex lens L17 that focuses it to a smaller area that lies on the monitor photodiode surface. Any reflections from the photodiode surface have to pass through F6 and F5 where they are further attenuated; this arrangement prevents any significant reflections from the monitor arm from re-entering the retinal-viewing path.

The Retinal Viewing System

Figure 7:
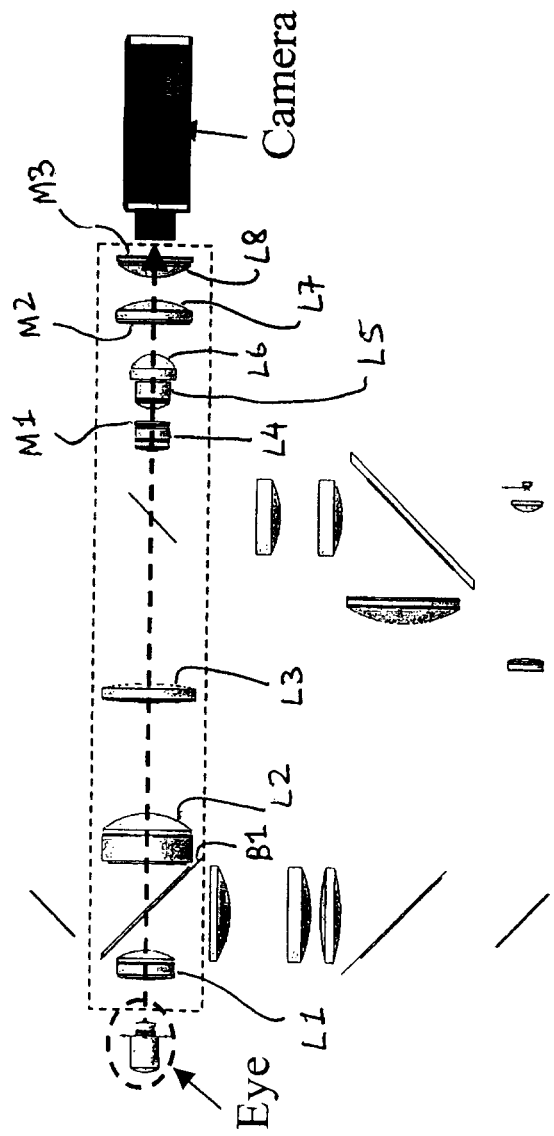
FIG. 7 is an illustration of the optical path during retinal imaging according to an embodiment.

The retinal viewing system is shown in FIG. 7. Light reflected from the retina exits the eye through the pupil and then is collected by the biconvex objective lens L1. It then passes through the main beam splitter B1. The light is then relayed through the lens doublet L2 and a biconvex lens L3. At this point, the light is in a relatively large area, collimated mode. It then passes to the final lens group or camera objective group consisting of the plano-convex lens L4, two plano-convex lenses L5 and L6, and two further plano-convex lenses L7 and L8. A mask M1 is inserted between L4 and L5. This blocks the reflection from the cornea. A second mask M2 is inserted between L6 and L7. This blocks the reflection from the nearer surface of L1. A third mask M3 is inserted between L7 and L8. This blocks the reflection from the outer surface of L1.

The camera is moveable on its axis and its position is controlled by a motor. This movement is used to compensate for the prescription of the patient, to optimize the focus as a function of wavelength, and to optimize the focus under the control of the operator who is viewing a live video representation of the fundus. The nominal magnification ratio from retina to CCD has a value of 1.25.

The Corneal Viewing System

Figure 8:
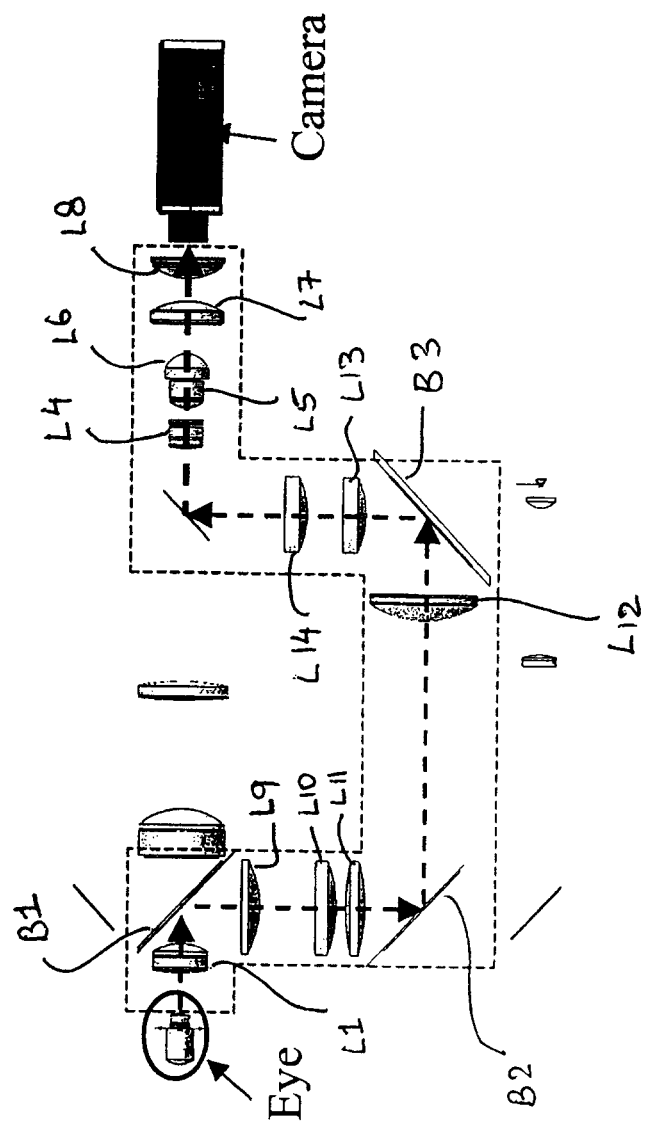
FIG. 8 is an illustration of the optical path during corneal imaging according to an embodiment.

The corneal viewing system is shown in FIG. 8. Note that the same camera is used both for corneal and retinal viewing. To switch from one mode to the other, the reflector R1 is moved; in one position, the retinal viewing path is unobscured while in the other position, the camera view is deflected into a vertical path containing L13 and L14. The two viewing modes are arranged such that they are co-axial—that is when the optical head is aligned, the centre of the cornea and the centre of the retinal view appear at the same location of the CCD.

The corneal viewing path begins with the biconvex lens L1. Light is diverted at the main beam splitter B1 and travels down through the lenses L9, L10 and L11 to the second beam splitter B2. A small proportion of the light, typically about 8%, reflects off B2 and passes through the lens L12 to the dichroic beam splitter B3. At B3, the infrared light used for corneal viewing is almost wholly reflected up through the lenses L13 and L14 after which it reflects off R1. From this point, it follows the same path as the retinal viewing system, passing through the camera objective group to the CCD. The nominal magnification ratio from cornea to CCD has a value of 1.0.

The Fixation Target Screen System

Figure 9:
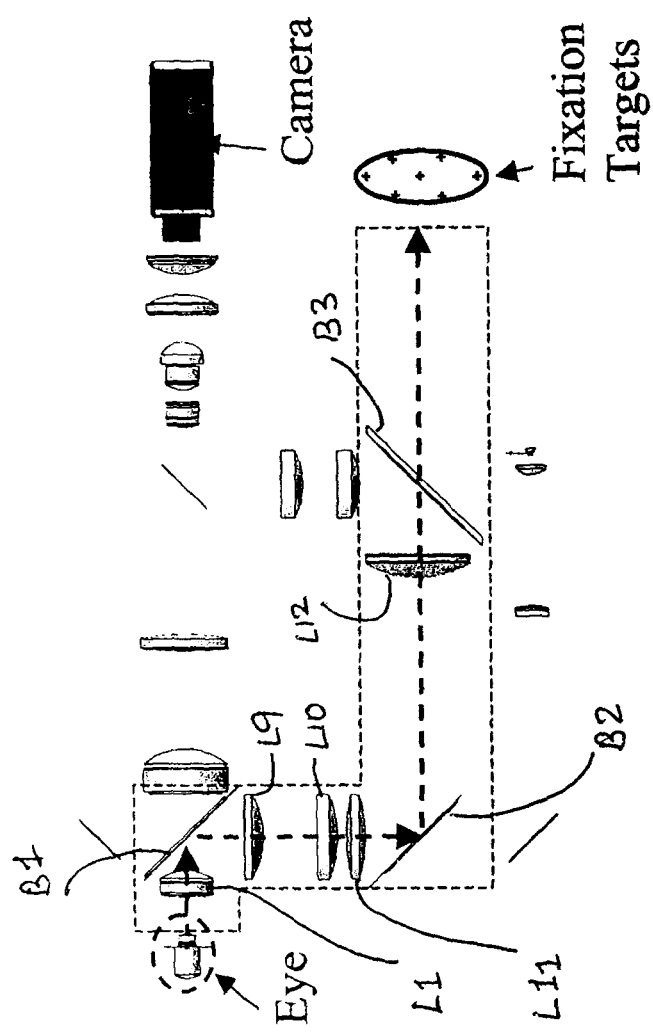
FIG. 9 is an illustration of the optical path during fixation of targets according to an embodiment.

The fixation target screen system is shown in FIG. 9. The viewing path is the same as that of the corneal viewing path described above, with the exception that at the dichroic beam splitter B3, the visible light from the targets screen display passes through. The target screen, in an embodiment, consists of a white surface marked up with seven fixation target crosses, one in the centre and six evenly spaced around the periphery.

The surface of the target screen is front-lit by a white LED. Behind each cross is a red LED that is activated when that cross is to be used as the fixation target. This causes the cross to have a red backlight. The power from the white LED can be varied to control the pupil opening to some extent.

It is possible to use a dynamic target screen such as that provided by an LCD display. This would place the operation of fixation target location wholly under the control of imaging software.

Exemplary Sequence of Operations

Figure 10:
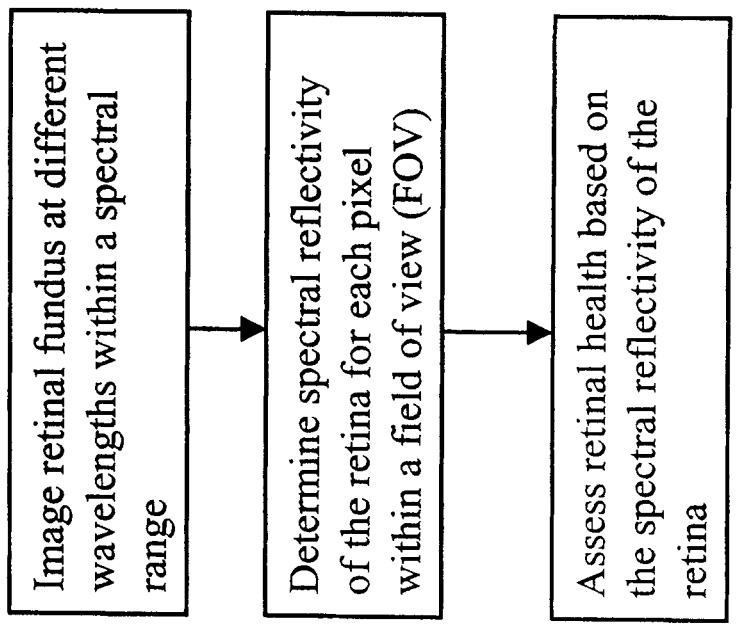
FIG. 10 is a flowchart showing the method of quantitative imaging of the retinal fundus according to an aspect of the present invention.

The following sequence of operations applies to the operation of the exemplary embodiment of the instrument. Generally, the method for quantitative imaging the retinal fundus is illustrated in FIG. 10. The method for retinal health assessment comprises imaging the retinal fundus at different wavelengths within a spectral range and determining spectral reflectivity of the retina for each pixel within a field of view (FOV). The retinal health is assessed based on the spectral reflectivity of the retina.

A patient is seated comfortably and places the forehead against the forehead brace and the chin on a chinrest of the instrument. The cardiac pulse sensor is placed at a suitable position on the patient; for example, the cardiac sensor is wrapped around a finger. The instrument is then put in the corneal viewing mode. Reflector R1 is placed in position and the corneal illuminating LEDs are activated. A fixation target is selected and illuminated and the patient is asked to gaze at the fixation target.

An operator adjusts the position of the optical head to centre the eye on the viewing axis and to set the correct working distance. The camera captures a view of the cornea, which is used to estimate the pupil size.

The instrument is then switched into the retinal-viewing mode. R1 is removed from the optical path and the corneal LEDs are extinguished. The infrared LED for illuminating the retina for focusing is activated. The operator optimizes the focus of the retina using the monitor. Once the focus is optimized, the retinal image capture sequence starts.

The pulsed infrared (IR) LED is coupled into the periscope port. Upon the heartbeat, the IR LED is pulsed for 4 milliseconds. During this time, the fixation illumination is extinguished. The CCD is actively storing photoelectrons during the image capture phase. At the end, the image charges are transferred into CCD storage and serially transferred out of the chip. The images are digitized and the results placed in a temporary store. The image data is then transferred by a suitable connection to the computer and digitally stored.

The periscope rotates and brings the red port into view. Upon the next heartbeat, the red LED is pulsed. The same sequence as above is followed and is repeated for the other LEDs (green, cyan and blue).

For auto-fluorescence imaging, the appropriate exciting LED is coupled to the illumination path using the rotating periscope. Then a blocking filter F1 is inserted into the viewing path. The CCD can be set to the 2×2 binning mode to enhance the signal to noise ratio. Then the image can be captured as above.

If additional information on the specular absorption is required, the retinal image capture sequence described above is repeated with another mask temporarily inserted.

The aforementioned steps may be repeated using the other eye of the patient. A similar sequence of imaging is used for the estimation of retinal oxygenation levels.

The computer performs multiple processing operations on the captured image data to prepare for presentation to the ophthalmologist who is typically using a remote PC connected to the instrument through Ethernet. The ophthalmologist is able to view images and to extract quantitative and qualitative data relating to the images.

In an exemplary embodiment, the instrument is capable of high-resolution digital multi-spectral retinal health assessment targeting research related to biochemical and structural retinal malfunction. The embodiment integrates a number of flexible measurement capabilities into a bench top instrument, which facilitates advanced clinical research measurements for monitoring the metabolic and anatomical activity of the eye to detect, at the earliest stage, activity that could lead to the onset of blinding eye diseases such as macular degeneration, diabetic retinopathy, glaucoma, cataracts, etc.

The exemplary embodiment targets the measurement of transient and persistent metabolic dysfunction, through advanced measurements of spatially resolved retinal oxygen saturation and retinal auto fluorescence. It enables the investigation of biochemical processes, and enhances the detection of drusen and other markers of RPE dysfunction through auto fluorescence and spectrally resolved fundus imaging at different wavelengths within a spectral range that spans from the visible region (about 450 nm) into the near infrared (NIR) region (about 1000 nm). In addition full color 40 degrees high-resolution fundus images provide correlation to clinical fundus photography. The embodiment can generate quantitative as distinct from qualitative data that can be used to more accurately gauge the health of the retina, particularly where such measurements are carried out at different time intervals and would allow trend analysis related to health degradation. The quantitative data will represent the spectral reflectivity of the retina for each pixel within the field of view (FOV).

Software control of all instrument functions provides flexible acquisition design with his quality and throughput providing value to both the subject (or patient) and the researcher. Data is presented on high-resolution displays and raw data are available in a number of formats for transfer into most data management and analysis instruments. The files and clinical instruments can be exported, for example, in industry standard DICOM format for incorporation into existing patient databases.

The exemplary embodiment provides integration of sophisticated and novel measurement capabilities, system control, and data analysis and management and data processing capabilities. The capabilities and features of the exemplary embodiment are described below.

Choroidal oxygenation is mapped across a 40 degree retinal field centered on the fovea with better than 30 μm lateral resolution. A signal extraction method enables oxygenation mapping equivalent to full spectral measurement with a finite number of wavelengths, resulting in shorter measurement times while maintaining accuracy and resolution.

The exemplary embodiment provides spectrally controlled stimulation and spectrally resolved detection of retinal auto fluorescence with up to 20 μm resolution across the 40 degree retinal field. Long term RPE function disruption can be mapped through quantitative lipofuscin distribution and drusen density analysis across the 40 degree field of the auto fluorescence retinal image. Researchers and users can refine their auto fluorescence analysis through easy access of the spectrally resolved images of auto fluorescence.

Research into retinal disease and abnormality is facilitated through spectrally resolved fundus imaging obtained using a series of narrow-band illumination sources spanning the full spectrum from 450 to 1000 nm. Spectrally resolved imaging has been shown to an effective way to enhance details and document absorption and scatter functions of the retina that can be correlated to retinal dysfunctions.

The exemplary embodiment can automatically combine images taken at different illumination wavelengths to produce a high-resolution RGB-standard color fundus image.

An optimized GUI-based user interface on the high-performance computer platform provided with the exemplary embodiment allows for intuitive control over the functions of the instrument. Data entry windows allow seamless integration of custom measurement parameters, such as setting of illumination intensities and saving commonly used experimental configurations. Use of standard file format, such as DICOM standard, ensures reliable data and subject information management across multiple platforms using different instrument configurations.

The software used in the exemplary embodiment provides secure and effective management of the acquired image data and subject or patient information. Spectral slicing, false color, automatic and manual balancing, zoom, pan, etc., are all controlled from the host computer and displayed on a high-resolution display, such as a LCD monitor.

The exemplary embodiment can be packaged as a robust tabletop instrument, designed for simple placement and positioning. The remote AC power adaptor and computer/controller enable optimum experimental flexibility while the integrated sensing units maintain reproducibility over time. The modular design allows for easy maintenance.

The level of integration in the exemplary embodiment provides a highly effective and flexible instrument for advanced investigation of retinal functions through fundus imaging and metabolic activity monitoring. The capability allows researchers to configure and control experiments with high quality and reproducible results.

The exemplary embodiment measures retinal health by monitoring metabolic activity through oxygenation and auto fluorescence of accumulated retinal by product. The instrument is a spatially resolved oxymeter with multiple narrow-band illumination sources; auto fluorescence lipofuscin and drusen camera with multiple filters and multiple stimulation frequencies; and a high resolution fundus camera, for example, 4 mega pixel for each wavelength with a working distance of about 20 mm in a room illumination of 10 lux and having a pupil diameter of 3.5±0.5 mm with a beam diameter of about 1 mm at cornea. The angle of coverage (circular) is about 40 degrees, and the wavelength range for detection is 450-1000 nm. The typical spectral resolution is 5 to 50 nm (FWHM) and the spatial resolution is about 30 μm for oxymetry. The acquisition time is about 4-8 millisecond per image as determined by the illumination flash duration and the acquisition timing is synchronized with heart pulse. The spatial resolution for auto fluorescence is about 20 μm and the dynamic range is about 40 dB and the wavelength detection is about 500 to 1000 nm in spectral bands. The total number of spectral points is a minimum of 4 and minimum detectable intensity change is of the order of 1% for each wavelength band. The patients apparent viewing range is focused on infinity with adjustment for presbyopia. The spatial resolution on the retina for the full color fundus camera is about 20 μm. The illumination levels conform to class 1 ANSI Z136 standard. The instrument can be controlled with standard operating systems such as Windows® and the image data conform to standards such as DICOM, jpeg, tiff, bitmap, etc. Additional adjustments include vertical and lateral adjustment to center dark pupil; two point source reflections minimized to set correct working distance of 20 mm; lighting adjusted to optimize pupil size; automatic coarse focus using patient's prescription accommodating a range of ±16 diopters; and automatic optimization for each wavelength. The exemplary embodiment also provides live image of cornea with off-axis IR illumination; a sequence of illumination pulses each synchronized to the cardiac pulse; corneal image capture to automatically calculate pupil area; live retinal view under IR illumination with manual fine focus; an illumination cone angle of about 43~47 degrees; and an image capture cone angle of about 41~45 degrees. The cold instrument warm up time is typically less than 10 minutes and standby warm time is typically less than 1 minute. The typical total illumination energy is of the order of 50 μJ with a per pixel illumination energy is about 42 pJ. The photon count on the retina is about 115 million per pixel while the photoelectron count at the CCD is about 15000 per pixel. A typical limiting value for sensor resolution is about 1.3 arcmin or about 6.5 μm.

The embodiments of the instrument described herein are capable of several types of measurement, including mapping retinal spectral reflectivity, measuring interior specular absorption, and mapping retinal auto-fluorescence and retinal oxygenation measurements. Thus, the instrument has greater value to the ophthalmologist who would otherwise have to invest in additional instruments, if available, and devote more time to patient care.

In the preceding description, for purposes of explanation, numerous details are set forth in order to provide a thorough understanding of the embodiments of the invention. However, it will be apparent to one skilled in the art that these specific details are not required in order to practice the invention. In other instances, well-known electrical structures and circuits are shown in block diagram form in order not to obscure the invention. For example, specific details are not provided as to whether the embodiments of the invention described herein are implemented as a software routine, hardware circuit, firmware, or a combination thereof.

Embodiments of the invention can be represented as a software product stored in a machine-readable medium (also referred to as a computer-readable medium, a processor-readable medium, or a computer usable medium having a computer-readable program code embodied therein). The machine-readable medium can be any suitable tangible medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the invention. Those of ordinary skill in the art will appreciate that other instructions and operations necessary to implement the described invention can also be stored on the machine-readable medium. Software running from the machine-readable medium can interface with circuitry to perform the described tasks.

The above-described embodiments of the invention are intended to be examples only. Alterations, modifications and variations can be effected to the particular embodiments by those of skill in the art without departing from the scope of the invention, which is defined solely by the claims appended hereto.

The invention claimed is:

1. A method for retinal health assessment comprising:
imaging the retinal fundus of a patient's eye at different wavelengths within a spectral range by illuminating the retinal fundus with an illuminating light energy;
determining spectral reflectivity of the retina for each pixel within a field of view (FOV) by comparing, for each pixel, the illuminating light energy with a reflected light energy on the basis of specular retinal reflectivity and diffuse retinal reflectivity data of the retinal fundus image; and
assessing retinal health based on the spectral reflectivity of the retina.

2. The method of claim 1, wherein
the step of imaging comprises capturing a sequence of substantially mono-spectral retinal images; and
the step of determining the spectral reflectivity of the retina comprises an analysis of the sequence of substantially mono-spectral retinal images.

3. The method of claim 1, wherein the imaging is through a pupil of the patient's eye and includes:
illuminating the retinal fundus through a central region of the pupil; and
detecting reflected light through an annular region surrounding the central region.

4. The method of claim 3, further comprising:
measuring a total area of the pupil; and
normalizing the reflected light energy to determine the spectral reflectivity of the retina independent of the total area of the pupil.

5. The method of claim 3, further comprising:
obtaining surface topology information of various reflective layers of the retina for assessing the retinal health.

6. The method of claim 3, wherein the step of illuminating the retinal fundus comprises:
illuminating the retinal fundus using polarized light; and
analyzing polarimetrically the reflected light from the retina to determine the spectral reflectivity of the retina.

7. The method of claim 1, further comprising:
determining a retinal auto-fluorescence factor by illuminating the retinal fundus at a first wavelength and imaging the retinal fundus at a second wavelength equal to an auto-fluorescence wavelength of the fundus; and
assessing the retinal health based on the retinal auto-fluorescence factor.

8. The method of claim 1, further comprising:
determining retinal oxygenation by measuring the spectral reflectivity of the retinal fundus at two or more predetermined wavelengths; and
assessing retinal health based on the retinal oxygenation.

9. The method of claim 1, wherein the step of imaging the retinal fundus is performed by using substantially mono-spectral light emitting diode (LED) illumination sources.

10. The method of claim 1, wherein the step of imaging the retinal fundus is performed by using a narrowband of spectral radiation.

11. The method of claim 1, wherein the step of imaging comprises
illuminating the retinal fundus with substantially mono-spectral light; and
blocking preselected reflections of the substantially mono-spectral light by placing masks along an imaging path.

12. A retinal health assessment system comprising:
an optical unit for imaging the retinal fundus of a patient's eye at different wavelengths within a spectral range by illuminating the retinal fundus with an illuminating light energy; and
a processor for determining spectral reflectivity of the retina for each pixel within a field of view (FOV) by comparing, for each pixel, the illuminating light energy with a reflected light energy on the basis of specular retinal reflectivity and diffuse retinal reflectivity data of the retinal fundus image, and assessing retinal health based on the spectral reflectivity of the retina.

13. The system of claim 12, further comprising:
a cardiac sensor for coordinating the imaging of the retinal fundus with a cardiac cycle of the patient.

14. The system of claim 12, further comprising:
a processing means for distinguishing between specular retinal reflectivity and diffuse retinal reflectivity.

15. The system of claim 12, further comprising:
a plurality of illumination sources coupled to the optical unit in a rotating periscope arrangement for selective individual alignment with an illumination path of the optical unit.

16. The system of claim 12, wherein each of the plurality of illumination sources comprises a substantially mono-spectral LED illumination source.

17. The system of claim 12, further comprising:
one or more fixation targets for fixing the patient's gaze during imaging.

18. The system of claim 12, further comprising:
one or more optical masks to block preselected reflections in an imaging path of the optical unit.

19. The system of claim 12, further comprising:
a display connected to the processor for displaying retinal health assessment data generated by the processor.

20. The system of claim 12, further comprising:
a position controller for adjusting a position of the optical unit during imaging for alignment with the imaging path relative to the patient's eye.

* * * * *